United States Patent [19]

Huber

[11] 4,295,854
[45] Oct. 20, 1981

[54] APPARATUS AND METHODS FOR SAMPLE ENRICHMENT FOR FLAMELESS ATOMIC ABSORPTION SPECTROSCOPY

[75] Inventor: Bernhard Huber, Uberlingen, Fed. Rep. of Germany

[73] Assignee: Bodenseewerk Perkin-Elmer & Co., GmbH, Fed. Rep. of Germany

[21] Appl. No.: 78,367

[22] Filed: Sep. 24, 1979

[30] Foreign Application Priority Data

Jan. 29, 1979 [DE] Fed. Rep. of Germany ....... 2903246

[51] Int. Cl.³ .......................... G01J 3/02; G01N 31/02
[52] U.S. Cl. ................................ 23/230 PC; 356/36; 356/312; 422/80
[58] Field of Search ................ 73/422 GC; 422/80; 23/230 PC; 356/36, 312

[56] References Cited

U.S. PATENT DOCUMENTS

| | | | |
|---|---|---|---|
| 3,662,604 | 5/1972 | Low et al. | 73/422 GC X |
| 3,671,129 | 6/1972 | Wiedeking | 356/312 |
| 3,681,212 | 8/1972 | McKissick | 204/45 R X |
| 3,824,016 | 7/1974 | Woodriff et al. | 356/312 |
| 4,111,051 | 9/1978 | Tamm et al. | 73/422 GC X |

OTHER PUBLICATIONS

Publ. . . . "Pre-Electrolysis with . . . Absorption Spectrometry . . . etc." by G. Torsi Annalic de Chimica 67/1977 pp. 557–566.

Primary Examiner—Daniel M. Yasich
Attorney, Agent, or Firm—S. A. Giarratana; F. L. Masselle; R. A. Hays

[57] ABSTRACT

Disclosed are methods and apparatus for concentrating a looked-for element from a solution for flameless atomic absorption spectroscopy. The tip of an electrode is dipped into a sample vessel containing the solution and an electric current is passed through the electrode and solution to electrodeposit the components of the solution on the electrode. The electrode with the electrodeposition is removed from the sample vessel and inserted into the graphite tube. The tube is then heated and the sample components electrodeposited on the electrode are atomized for analysis by the measuring beam of the atomic absorption spectrometer.

14 Claims, 4 Drawing Figures

APPARATUS AND METHODS FOR SAMPLE ENRICHMENT FOR FLAMELESS ATOMIC ABSORPTION SPECTROSCOPY

BACKGROUND OF THE INVENTION

The present invention relates to apparatus and methods for concentrating a looked-for element from a solution for flameless atomic absorption spectroscopy, wherein the looked-for element is deposited on a carrier by electrolysis, and the carrier, with the electrodeposition, is heated in the path of rays of an atomic absorption spectrometer to atomize the deposited components.

In flameless atomic absorption spectroscopy, a metered portion of a sample is disposed in a graphite tube. The graphite tube is radiated in a longitudinal direction by the measuring beam of an atomic absorption spectrometer. The measuring beam consists of light having the resonance wavelength of the looked-for element. The graphite tube is heated to a high temperature by electric current. The sample is thus decomposed and vaporized (atomized), whereby the elements of the sample are present in the graphite tube in their atomic states in a "cloud of atoms". The measuring beam, which, as mentioned above, consists of light having the resonance wavelength of the looked-for element, is absorbed in accordance with the quantity of the looked-for element in the sample, as each element in its atomic state absorbs its resonance wavelength only.

This measurement can be disturbed by smoke, which forms when the sample is vaporized, and which results in absorption of the measuring beam. If the smoke develops at the same temperature at which the looked-for element vaporizes, measurement may sometimes become impossible.

To avoid these problems, it is known to deposit the looked-for element by electrolysis from a sample solution in a graphite crucible (Annali di Chimica, 67 (1977), pages 557 to 566). In this method, a crucible of glassy carbon is used, and is supported between two graphite rods below the path of the rays of the measuring beam of an atomic absorption spectrometer. A circulation system with two coaxial small connecting sockets opens into the graphite crucible. In this manner a sample is pumped into and suctioned from the crucible. During its flow through the crucible, the sample solution is subjected to electrolysis, the crucible constituting one electrode for the electrolysis on which, for example, metals are deposited.

Subsequently, a washing solution is flushed through the crucible, and the circulation system is removed. The crucible is then heated by an electric current, whereby the deposited electrodeposition is vaporized and displaced into the path of rays of the atomic absorption spectrometer as a cloud of atoms.

The above described method requires a relatively expensive apparatus and, because of the necessity of circulating the sample solution, requires a relatively large sample quantity. The whole procedure takes place within the atomic absorption spectrometer. The cloud of atoms forms in free space above the crucible and is therefore dissipated very quickly due to diffusion. This method would not be applicable with a graphite tube.

SUMMARY OF THE PRESENT INVENTION

Accordingly, it is a primary object of the present invention to provide apparatus and methods for concentrating a looked-for element from a solution for flameless atomic absorption spectroscopy wherein the concentrated sample is atomized within a graphite tube.

It is another object of the present invention to provide apparatus and methods for concentrating a looked-for element from a solution for flameless atomic absorption spectroscopy by the process of electrolytic enrichment.

It is still another object of the present invention to provide apparatus and methods for concentrating a looked-for element from a solution for flameless atomic absorption spectroscopy by process of electrolytic enrichment and elimination within the heated graphite tube of unwanted matrix components.

It is a further object of the present invention to provide apparatus and methods for concentrating a looked-for element from a solution for flameless atomic absorption spectroscopy located external to the atomic absorption spectrometer and as an excessory thereto.

It is a still further object of the present invention to provide apparatus and methods for concentrating a looked-for element from a solution for flameless atomic absorption spectroscopy which is accomplished by simple apparatus and methods and which may be automated.

Additional objects and advantages of the present invention will be set forth in part in the description which follows, and in part will be obvious from the description, or may be learned by practice of the invention. The objects and advantages of the invention may be realized and obtained by means of the instrumentalities and combinations particularly pointed out in the appended claims.

To achieve the foregoing objects and in accordance with the purpose of the present invention, as embodied and broadly described herein, a method for concentrating a looked-for element from a solution for flameless atomic absorption spectroscopy comprises the steps of: inserting an electrode into a sample vessel containing the solution, passing an electric current through the electrode and the solution whereby the components of the solution including the looked-for element are deposited on the electrode, removing the electrode with the electrodeposited looked-for element carried thereby from the sample vessel and inserting the electrode into the graphite tube through which the measuring beam of an atomic absorption spectrometer passes, and heating the graphite tube, whereby the electrode is heated and the sample components deposited thereon are atomized.

In a further aspect of the present invention and to further achieve the foregoing objects, apparatus for concentrating a looked-for element from a solution for flameless atomic absorption spectroscopy comprises a graphite tube atomizer having a graphite tube and a lateral bore through the tube, a sample vessel for containing a sample liquid, a pair of terminals for connection to a source of current, sample feeding means for removing sample from the sample vessel including a first electrode of electrically conductive material and connected to one of the pair of terminals and a second electrode connected to the other of the pair of terminals and in electrically conductive contact with the sample liquid in the sample vessel, and an actuator for moving the sample feeding means into and out of the sample vessel and into the lateral bore of the graphite tube.

Thus, in accordance with the apparatus and methods of the present invention, neither a graphite crucible nor a graphite tube itself is used as an electrode for electrolysis, on which sample substance including the looked-for element is deposited. Rather, a separate electrode is used, which is inserted into the sample vessel and on which the looked for element is deposited. This electrode is then moved mechanically into the graphite tube and is heated with the graphite tube to form the cloud of atoms.

The invention consists in the novel parts, constructions, arrangements, combinations and improvements shown and described. The accompanying drawings which are incorporated in and constitute a part of this specification, illustrate one embodiment of the invention and together with the descriptions serve to explain the principles of the invention.

DETAILED DESCRIPTION OF A PREFERRED EMBODIMENT

Reference will now be made in detail to the present preferred embodiment of the invention, an example of which is illustrated in the accompanying drawings.

Figure 1:
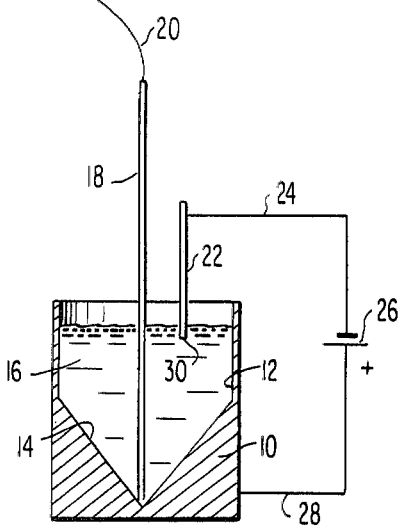
FIG. 1 is a schematic representation of an apparatus for concentrating a looked-for element from a solution for flameless atomic absorption spectroscopy in accordance with the present invention.

Referring now to the drawings, and particularly to FIG. 1, a sample vessel, designated 10, is comprised of a cylindrical wall 12 and a concave-conical bottom 14. Sample vessel 10 accommodates a solution 16, which contains the looked-for element. A gas supply tube 18 is connected to a source of inert gas, not shown, through a conduit 20. By means discussed hereinafter, tube 18 is mounted for vertical movement into sample vessel 10 and into solution 16 to the extent its tip may be spaced a distance slightly elevated from the concave-conical bottom 14. An electrode 22 of an electrically conductive, highly temperature resistant material, is carried by a lever 54 such that the tip only of electrode 22 dips into the solution 16. Electrode 22 is connected through a conductor 24 to the negative terminal of a direct current source 26. The positive terminal of direct current source 26 is connected through a conductor 28 to sample vessel 10, which is also formed of electrically conductive material.

In this way, an electrolysis of solution 16 in vessel 10 may take place. Electrode 22 acts as a cathode to which the positively charged cations, for example the metals, migrate for deposition thereon. In this embodiment, the anode constitutes the electrically conductive sample vessel 10. By supplying inert gas through gas supply tube 18 into the bottom 14 of the chamber defined by sample vessel 10, solution 16 is continuously stirred. This insures that the quantity of sample substances deposited during a predetermined time period is representative of the concentration of these substances in solution 16.

Figure 2:
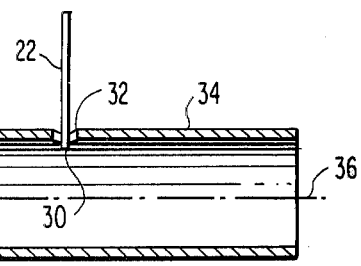
FIG. 2 is a vertical cross-sectional view through a graphite tube illustrating the electrode with the sample electrode deposited thereon in the graphite tube.

After certain sample substances, for example metals including the looked-for element, have been deposited on the tip of electrode 22, electrode 22 is removed from sample vessel 10 and from solution 16, rinsed, and then inserted, with its tip 30 bearing the electrode deposition, into a lateral bore 32 of a graphite tube 34. To this end, electrode 22 is rod shaped and only its tip 30 is dipped into solution 16. The tip 30 of electrode 22 with the electrode deposition is inserted into the lateral bore 32 of the graphite tube 30 such that its tip is located closely adjacent lateral bore 32 as illustrated in FIG. 2 when the graphite tube 34 is heated by means 35 which can be conventional graphite tube heating electrodes.

When the graphite tube is heated, electrode 30 is heated indirectly and the sample components deposited on its tip are atomized. Thus, a cloud of atoms is formed within the graphite tube 34 and through which the measuring beam 36 is passed as illustrated in FIG. 2.

Figure 3:
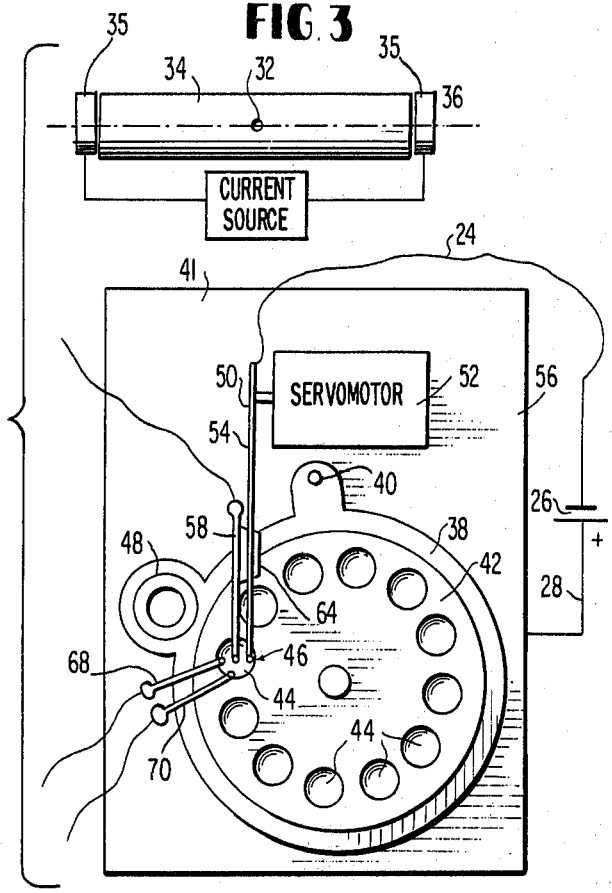
FIG. 3 is a plan view of apparatus for concentrating the looked-for element from a solution and feeding the concentrated sample from a sample vessel to the graphite tube.
Figure 4:
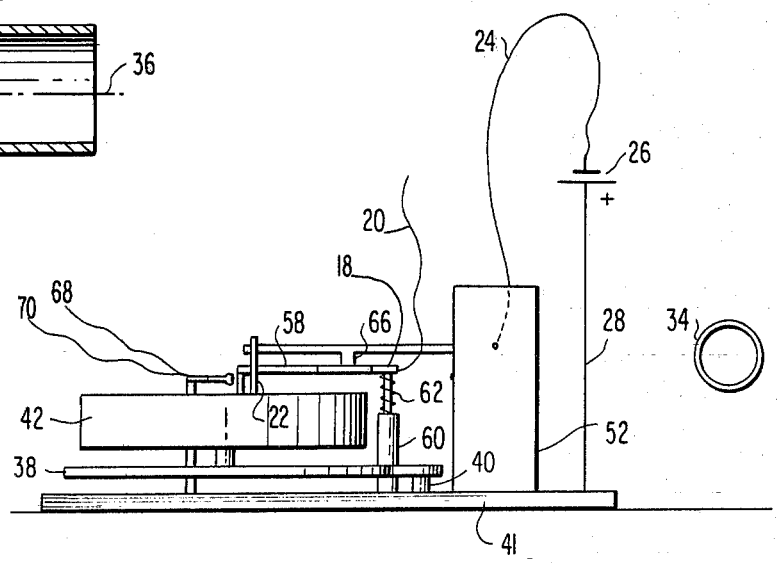
FIG. 4 is a side elevational view thereof.

The foregoing described apparatus and method may be automated as illustrated in FIGS. 3 and 4. In the embodiment of FIGS. 3 and 4, a carrier plate 38 is pivotally mounted for rotation about a pivot axis 40 on a base plate 41. Carrier plate 38 carries a turntable 42, on which a circular array of sample vessels 44 is carried for rotation about the axis of rotation of turntable 42. The sample vessels 44 may be identical or similar to the vessel 10 illustrated in FIG. 1. A respective one of the sample vessels 44 is located at a predetermined operative location or station 46. A rinsing vessel 48, through which a rinsing liquid continuously flows, is located laterally of the sample vessel 44 located at the operative station 46, and at the same distance or radius from the pivoted axis 40 as the sample vessel. The carrier plate 38 is movable by a suitable mechanism, not shown, such as a servomotor, between two end positions determined by stops, also not shown. In one of the end positions illustrated in FIG. 3, a sample vessel 44 is located at the operative station 46. In the other end position, in which the carrier plate 38 is rotated counterclockwise about pivot axis 40 as viewed in FIG. 3, the rinsing vessel 48 is located at the operative station.

An actuating mechanism 50 is mounted on base plate 41. The actuating mechanism 50 comprises a servomotor 52 arranged to swing or pivot a lever 54 between two end positions about an axis normal to the longitudinal centerline of the lever, lever 54 being rotatable through 180 degrees about its longitudinal axis by a mechanism, not shown, simultaneously with its swinging movement between its end positions.

Electrode 22 is attached to the end of swinging lever 54 and projects substantially at a right angle to the longitudinal axis of lever 54. In one end position of lever 54, electrode 22 dips into the sample or rinsing vessel 44 or 48 respectively, depending on which of these vessels is located at the operative station 46. In the other end position of lever 54, electrode 22 extends through the lateral bore 32 into the graphite tube 34 as illustrated in FIG. 2. The arrangement of the graphite tube in the atomic absorption spectrometer and of the sample feeding device 56 is such that the plane through which the lever 54 passes as it rotates or swings through 180 degrees between the operative station 46 and the graphite bore 32 also contains bore 32 and operative station 46, the bore 32 and the operative station 46 being equally distant from the axis of the servomotor 52. Electrode 22 is connected to the negative terminal of direct current source 26 through insulated conductor 24. The positive terminal of the direct current source is at ground potential, e.g. is connected to base plate 41 and the turntable 42. The sample vessels 44 are also at this potential.

Gas inlet tube 18, which is connected to an inert gas gas source through conduit 20, is carried by a horizontal arm 58. Arm 58 is guided for vertical reciprocating movement by a guide 60 and is arranged to be depressed together with gas supply tube 18 against the action of a spring 62. A lug 64 is provided on arm 58 and is engaged by a projection 66 on lever 54 when lever 54 approaches one end position. Upon further swinging movement of lever 54 toward its one end position, lever 54 engages arm 58 and both arms 58 and lever 54 move conjointly to move gas supply tube 18 and the tip of electrode 22 into the sample or rinsing vessel 44 or 48, respectively.

Two supply tubes 68, 70 are carried by the sample feeding device 56 for supplying known solutions of the looked-for substance. Tubes 68 and 70 extend over the sample vessel 44 at its operative station 46 whereby predetermined quantities of a known solution of the looked-for substance can be supplied by means of a pump, not shown.

Means, not shown, are provided to control actuator mechanism 50 and the carrier plate 38 to make the following movements: move the carrier plate 38 into a first end position illustrated in FIG. 3, move the electrode 22 into the sample vessel 44 located at the operative station 46, remove electrode 22 from the sample vessel 44 after electrolysis has been completed, move the carrier plate 38 counterclockwise into the other end position, dip the electrode 22 into the rinsing vessel 48 then located at the operative station 46, and remove electrode 22 from the rinsing vessel 48 and inserting it into the lateral bore 32 of graphite tube 34.

In operation, electrode 22 is inserted outside the atomic absorption spectrometer into sample vessel 44 containing the solution. Direct electric current from current source 26 is passed through the electrode 22 and through the solution, whereby components of the solution, including the looked-for element are deposited on electrode 22 by electrolysis. Electrode 22 is removed from sample vessel 44 and is inserted into the lateral bore 32 of graphite tube 34. Graphite tube 34 is heated in a conventional manner, whereby electrode 22 is heated indirectly and the sample components deposited thereon atomized. In the illustrated embodiment, direct current is passed through the electrically conductive sample vessel 44 which serves as the second electrode for passing electricity through the solution. The solution is agitated in the sample vessel during electrolysis by supplying inert gas through gas supply tube 18. Electrode tube 22 with the electrode deposition thereon is rinsed, after it has been removed from the sample vessel and before it is inserted into the graphite tube. This is accomplished by first displacing lever 54 to remove the tip of the electrode from the sample vessel, rotating the carrier plate 38 to locate the rinsing vessel in the operative station, and displacing lever 54 to immerse the tip of electrode 22 in the rinsing solution.

It is also desirable to add a predetermined quantity of the looked-for substance through a supply tube 68 or 70 after the absorption measurement, and to subsequently repeat the electrolysis and atomic absorption measurement. Such an addition method, known per se, permits elimination of the influences of matrix on the electrolysis.

The constructional design of the arrangement described is similar in certain respects to the sampling apparatus and methods disclosed in U.S. Pat. No. 4,111,051 issued Sept. 5, 1978 of common assignee herewith, although there it will be appreciated that the sample is not concentrated prior to insertion into the graphite tube.

The present invention may be modified in various ways without departing from the scope or spirit of the invention. For example, the agitation of the solution in the sample vessel may be effected by means of a stirrer instead of a gas stream. Instead of a circular array of sample vessels 44 on a turntable, a sample vessel may, for example, comprise an overflow vessel through which is flowed a continuous stream of the solution. In this way, a liquid stream can be monitored continuously. Also, the present invention can be achieved with the device of the type described by directing sample solution through the "rinsing vessel" 48, which would then serve as the sample vessel. To this end, the rinsing vessel would be formed of an electrically conductive material, for example glassy carbon. Also, "sample vessels" 44 would then be filled with rinsing liquid. Thus, in this manner the usual sample vessels formed of plastic material may be utilized.

Further, instead of making the sample vessel of electrically conductive material, the gas inlet tube 18 may be formed of an electrically conductive material and connected to the current source to serve as a second electrode whereby electricity is passed between the electrode 22 and tube 18 rather than between the electrode 22 and the sample vessel.

In the foregoing manner, it will be appreciated that the sample may be concentrated and measured utilizing a conventional graphite tube atomizer, removal of the graphite tube not being necessary. Higher sensitivity is also achieved in a graphite tube as compared with a crucible as discussed above. Also, the apparatus and methods of the present invention permit ready and easy automation, reduce the risk of cross contamination to a minimum, and is applicable to both flowing and individual samples.

It will be apparent to those skilled in the art that various modifications and variations can be made in the present invention without departing from the scope or spirit of the invention.

What is claimed is:

1. A method of forming an atomic cloud of a looked-for element in a graphite tube through which a measuring beam of an atomic absorption spectrometer may be passed for the flameless atomic absorption spectroscopic measurement thereof, said method comprising the steps of:

inserting an electrode into a sample vessel containing a solution including said looked-for element;

passing an electric current through said solution to deposit components of said solution, including said looked-for element, on said electrode;

transferring said electrode having said looked-for element electrodeposited thereon from said sample vessel to said graphite tube such that said graphite tube and said electrode are in a heat transfer relationship, said transferring step including inserting said tip of said electrode carrying said electrodeposition into said graphite tube, via a lateral bore in the wall thereof, such that said tip is located inside said graphite tube; and heating said graphite tube to a temperature whereat said components are atomized to form said atomic cloud.

2. The method according to claim 1 wherein said sample vessel is electrically conductive and said current is passed through said solution with said electrically conductive sample vessel serving as a second electrode.

3. The method according to claim 2 wherein said electrode on which said sample components are deposited is rod-shaped, and including dipping only the tip of said electrode into said solution.

4. The method according to claim 1 including continuously flowing a stream of solution through said sample vessel.

5. The method according to claim 1 including stirring said solution in said sample vessel during electrolysis.

6. The method according to claim 5 including introducing a gas stream into said solution adjacent the bottom of said sample vessel to stir said solution.

7. The method according to claim 1 including rinsing said electrode carrying said electrodeposition after its removal from said sample vessel and before its insertion into said graphite tube.

8. The method according to claim 1 including adding a predetermined quantity of said looked-for substance after said atomic absorption measurement, and thereafter repeating said electrolysis and said atomic absorption measurement.

9. Apparatus for forming an atomic cloud of a looked-for element from a solution for flameless atomic absorption spectroscopy comprising:
 a graphite tube having a lateral bore through the wall of said tube,
 a sample vessel for containing a sample solution
 a pair of terminals for connection to a source of current,
 means for removing components of said solution from said sample vessel including a first electrode of electrically conductive material connected to one of said pair of terminals and a second electrode connected to the other of said pair of electrodes, said second electrode being in electrically conductive contact with said sample solution in the sample vessel, whereby components of said solution can be electrodeposited on said first electrode;
 an actuator for moving said first electrode into and out of said sample vessel and into said lateral bore of said graphite tube;
 a carrier plate movable between two positions, a rinsing vessel and said sample vessel being carried by said carrier plate, said sample vessel being in an operative station in one position of said carrier plate and said rinsing vessel being in said operative station in another position of said carrier plate, said operative station being located to permit said first electrode to be dipped into said vessels by said actuator mechanism, and means for controlling the movements of said carrier plate and said actuator mechanism to move said carrier plate into one position, move said first electrode into said sample vessel located at the operative station, remove said first electrode from said sample vessel after electrolysis has been completed, move said carrier plate into said other position, dip said first electrode into said rinsing vessel located at the operative station, move said first electrode from said rinsing vessel, and insert said first electrode into said lateral bore of said graphite tube;
 a gas supply tube coupled to said first electrode for dipping into said sample or rinsing vessels, a source of inert gas, said gas supply tube being connected to said inner gas source when said first electrode is dipped; and
 means for heating said graphite tube to a temperature whereat said components are atomized to form said atomic cloud within said graphite tube.

10. Apparatus according to claim 9 including at least one supply tube for supplying a known solution of said looked-for substance and extending over said sample vessel at its operative station.

11. Apparatus according to claim 9 wherein said sample vessel has a concave bottom, said gas supply tube extending into said sample solution such that the tip of said tube is spaced close to but slightly above said concave bottom.

12. Apparatus according to claim 11 wherein said gas supply tube is electrically conductive and connected to the current source to serve as said second electrode for said electrodeposition.

13. Apparatus according to claim 9 including a horizontal arm carried for vertical movement, a spring for biasing said arm for vertical movement in one direction, said gas supply tube being carried by said horizontal arm and arranged for vertical movement with said gas supply tube against the bias of said spring, said actuator mechanism including a swinging lever, a servomotor for swinging said lever between two end positions and for rotating said lever simultaneously through 180° about its longitudinal axis, said first electrode being carried by said lever adjacent an end thereof and projecting substantially at right angles to the longitudinal axis of said lever, said first electrode in one end position of said lever dipping into the sample or rinsing vessels and extending into the graphite tube in the other end position of said lever, and a lug carried by said arm, said swinging lever engaging said lug when approaching its one end position and moving said gas supply tube into the sample or rinsing vessels respectively upon further movement of said lever toward said one end position.

14. Apparatus according to claim 9 wherein said sample vessel is comprised of electrically conductive material and is connected to said current source to serve as a second electrode for said electrodeposition.

* * * * *